(12) United States Patent
Burkholz

(10) Patent No.: US 8,439,877 B2
(45) Date of Patent: May 14, 2013

(54) BI-DIRECTIONALLY ENGAGEABLE CANNULA CRIMP FEATURE

(75) Inventor: Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 504 days.

(21) Appl. No.: 12/396,227

(22) Filed: Mar. 2, 2009

(65) Prior Publication Data
US 2010/0222745 A1  Sep. 2, 2010

(51) Int. Cl.
*A61M 5/178* (2006.01)
*A61M 5/00* (2006.01)

(52) U.S. Cl.
USPC .......... 604/164.08; 604/110; 604/164.12

(58) Field of Classification Search .......... 604/164.08, 604/110, 164.12
See application file for complete search history.

(56) References Cited

U.S. PATENT DOCUMENTS

| | | | |
|---|---|---|---|
| 4,846,811 A * | 7/1989 | Vanderhoof ............ 604/263 |
| 4,952,207 A | 8/1990 | Lemieux | |
| 4,964,854 A | 10/1990 | Luther | |
| 5,085,648 A | 2/1992 | Purdy et al. | |
| 5,135,504 A | 8/1992 | McLees | |
| 5,601,536 A | 2/1997 | Crawford et al. | |
| 5,833,670 A | 11/1998 | Dillon et al. | |
| 6,004,294 A | 12/1999 | Brimhall et al. | |
| 6,012,213 A | 1/2000 | Chang et al. | |
| 6,117,108 A | 9/2000 | Woehr et al. | |
| 6,224,569 B1 | 5/2001 | Brimhall | |
| 6,287,278 B1 | 9/2001 | Woehr et al. | |
| 6,322,537 B1 | 11/2001 | Chang | |
| 6,379,333 B1 * | 4/2002 | Brimhall et al. .......... 604/164.11 |
| 6,443,927 B1 | 9/2002 | Cook | |
| 6,443,929 B1 * | 9/2002 | Kuracina et al. ............ 604/192 |
| 6,616,630 B1 | 9/2003 | Woehr et al. | |
| 6,629,959 B2 | 10/2003 | Kuracina et al. | |
| 6,652,486 B2 | 11/2003 | Bialecki et al. | |
| 6,652,490 B2 | 11/2003 | Howell | |
| 6,663,592 B2 | 12/2003 | Rhad et al. | |
| 6,692,471 B2 | 2/2004 | Boudreaux | |
| 6,749,588 B1 * | 6/2004 | Howell et al. ............ 604/164.08 |
| 6,761,706 B2 | 7/2004 | Vaillancourt | |
| 6,860,871 B2 | 3/2005 | Kuracina et al. | |

(Continued)

FOREIGN PATENT DOCUMENTS

| | | |
|---|---|---|
| EP | 1 785 159 A1 | 5/2007 |
| WO | 02/45786 A2 | 6/2002 |

*Primary Examiner* — Theodore J Stigell
*Assistant Examiner* — Jenna Zhang
(74) *Attorney, Agent, or Firm* — Jeanne Lukasavage; Craig Metcalf; Kirton McConkie

(57) ABSTRACT

A cannula, such as an IV catheter introducer needle, that has a bi-directionally engageable crimp feature is described herein. The feature comprises a maximum outer diameter that is greater than an outer diameter of the cannula. Additionally, the feature comprises a proximal side and a distal side. The larger outer diameter of the proximal side can act as a proximal engagement that prevents the cannula from being entirely extracted in a proximal direction from a cannula shield. The distal side of the feature can comprise a notch that acts a distal engagement, which prevents the cannula from reemerging distally from the shield, once the cannula has been pulled into the shield. The notch can include an engagement surface that extends laterally past the cannula's outer diameter. The engagement surface can be configured to run substantially perpendicular to the cannula's longitudinal axis.

19 Claims, 12 Drawing Sheets

U.S. PATENT DOCUMENTS

| | | | |
|---|---|---|---|
| 6,914,212 B2 * | 7/2005 | Adams | 219/121.6 |
| 7,002,098 B2 | 2/2006 | Adams | |
| 7,160,269 B2 | 1/2007 | Woehr | |
| 7,186,239 B2 | 3/2007 | Woehr | |
| 7,214,208 B2 | 5/2007 | Vaillancourt | |
| 7,238,169 B2 | 7/2007 | Takagi et al. | |
| 7,264,613 B2 | 9/2007 | Woehr et al. | |
| 2002/0169418 A1 | 11/2002 | Menzi et al. | |
| 2003/0144627 A1 | 7/2003 | Woehr et al. | |
| 2004/0010227 A1 | 1/2004 | Riesenberger et al. | |
| 2004/0167472 A1 * | 8/2004 | Howell et al. | 604/164.01 |
| 2004/0186434 A1 | 9/2004 | Harding et al. | |
| 2004/0204681 A1 | 10/2004 | Thoresen et al. | |
| 2004/0225260 A1 | 11/2004 | Villa et al. | |
| 2004/0236288 A1 | 11/2004 | Howell et al. | |
| 2004/0243061 A1 | 12/2004 | McGurk | |
| 2005/0027263 A1 | 2/2005 | Woehr et al. | |
| 2005/0080378 A1 | 4/2005 | Cindrich et al. | |
| 2006/0116638 A1 | 6/2006 | Woehr et al. | |
| 2006/0270980 A1 | 11/2006 | Menzi et al. | |
| 2007/0100297 A1 | 5/2007 | Woehr et al. | |
| 2007/0129689 A1 | 6/2007 | Woehr et al. | |
| 2007/0156093 A1 | 7/2007 | Woehr | |
| 2007/0179446 A1 | 8/2007 | Carrez et al. | |
| 2007/0179447 A1 | 8/2007 | Carrez et al. | |

* cited by examiner

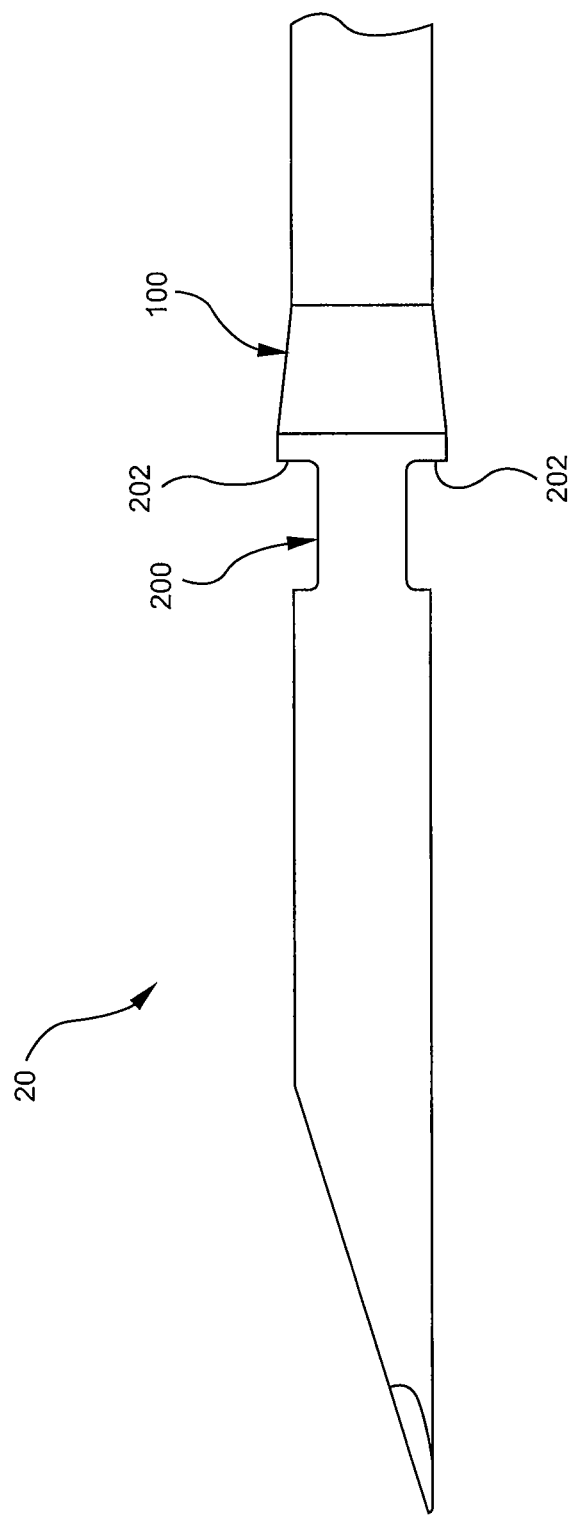

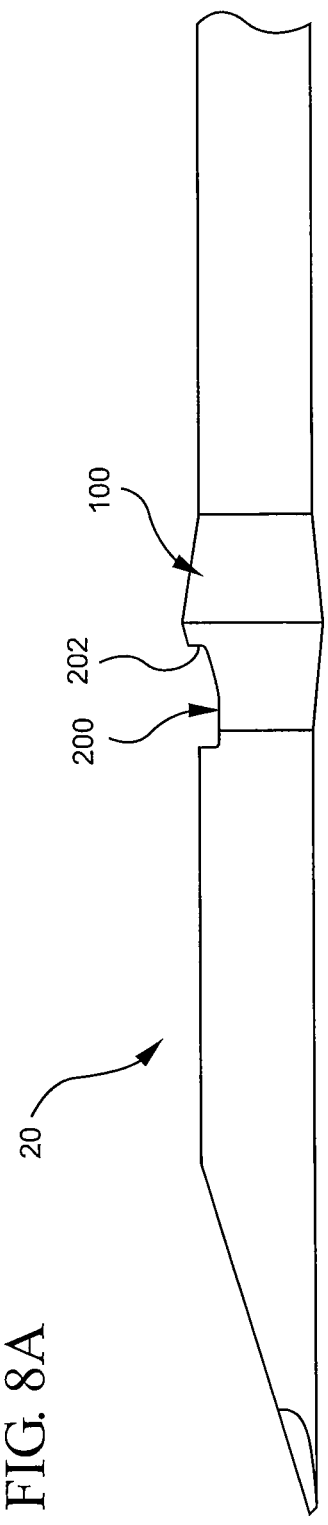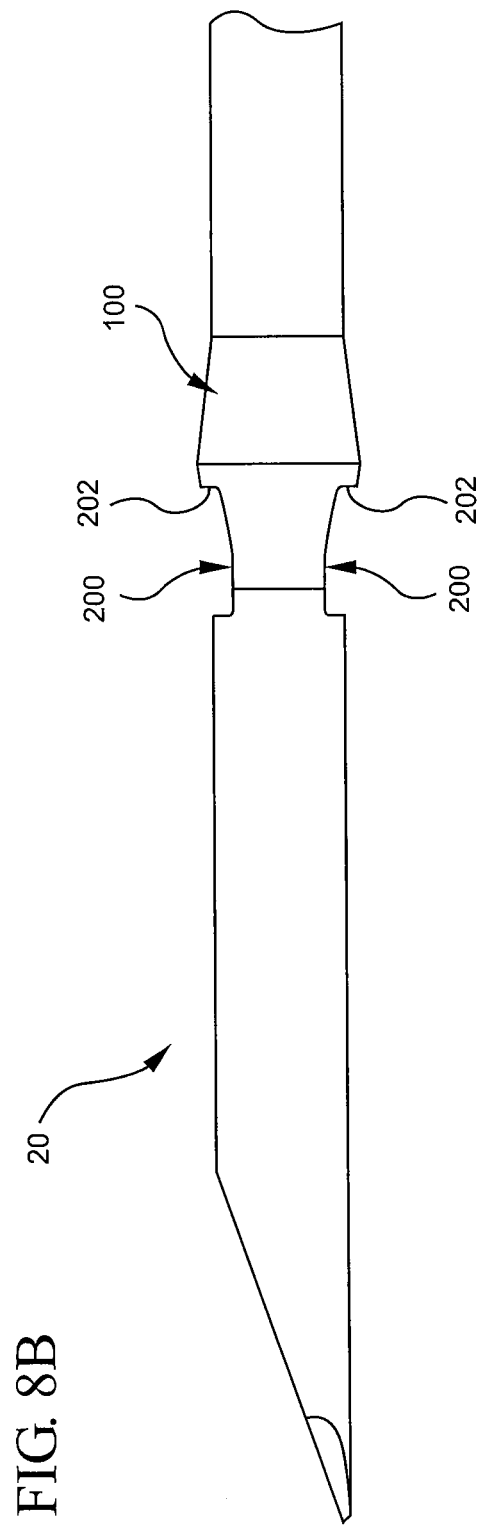
FIG. 8A
FIG. 8B

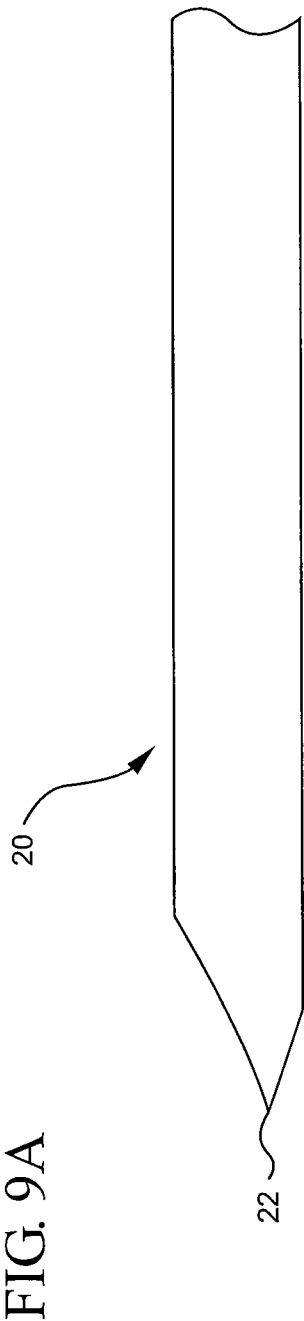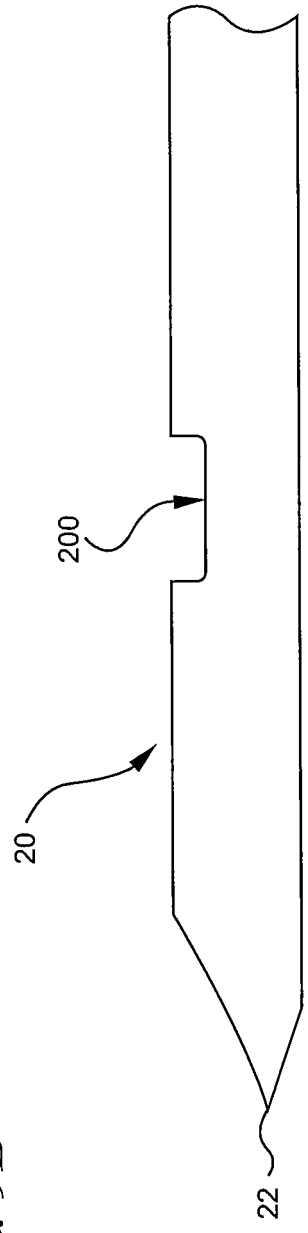
FIG. 9A
FIG. 9B

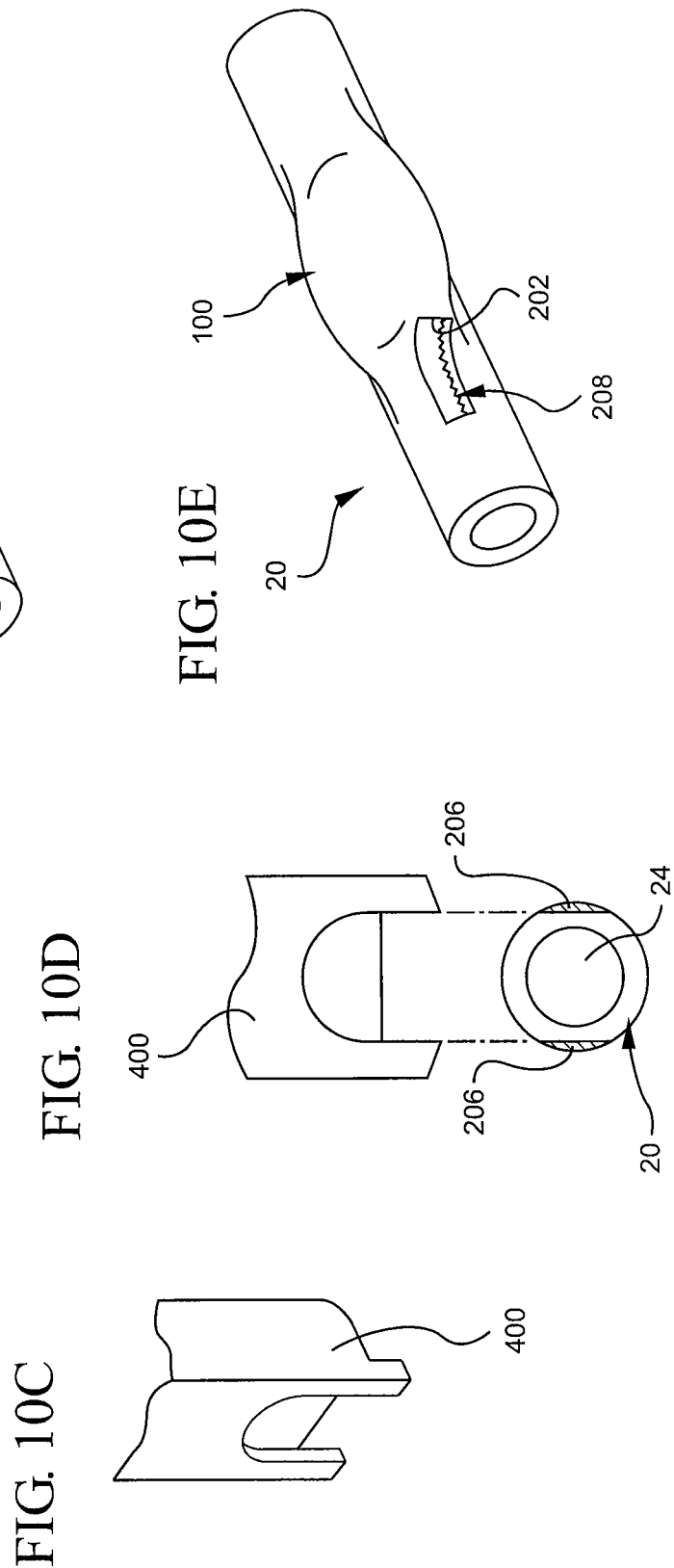

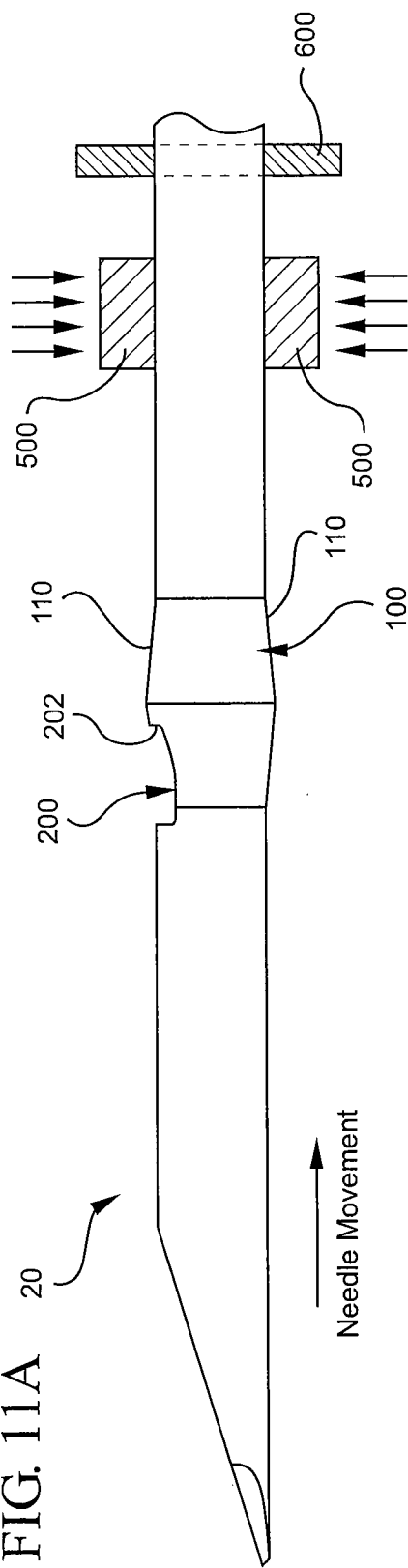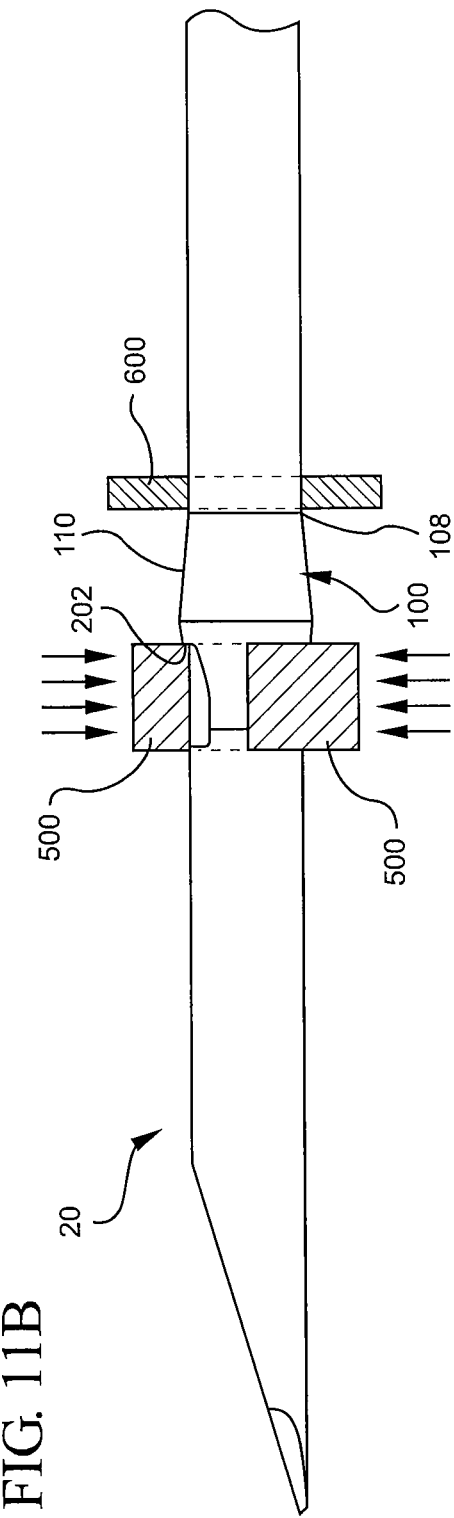

BI-DIRECTIONALLY ENGAGEABLE CANNULA CRIMP FEATURE

BACKGROUND OF THE INVENTION

This disclosure relates generally to vascular access devices and associated methods. More specifically, this disclosure discusses a cannula that comprises a bi-directionally engageable crimp feature. Such a cannula can be used with catheter assemblies.

Generally, vascular access devices are used for communicating fluid with the vascular system of patients. For example, catheters are used for infusing fluid (e.g., saline solution, medicaments, and/or total parenteral nutrition) into a patient, withdrawing fluids (e.g., blood) from a patient, and/or monitoring various parameters of the patient's vascular system.

Intravenous (IV) catheter assemblies are among the various types of vascular access devices. Over-the-needle peripheral IV catheters are a common IV catheter configuration. As its name implies, an over-the-needle catheter is mounted over an introducer needle having a sharp distal tip. The introducer needle is generally a hypodermic needle coupled to a needle assembly that helps guide the needle and facilitates its cooperation with the catheter. At least the inner surface of the distal portion of the catheter tightly engages the outer surface of the needle to prevent peelback of the catheter and, thereby, to facilitate insertion of the catheter into the blood vessel. The catheter and the introducer needle are often assembled so that the distal tip of the introducer needle extends beyond the distal tip of the catheter. Moreover, the catheter and needle are often assembled so that, during insertion, the bevel of the needle faces up, away from the patient's skin. The catheter and introducer needle are generally inserted at a shallow angle through the patient's skin into a blood vessel.

Once an operator has determined that the distal tip of the catheter is properly placed in the blood vessel, the operator may apply pressure to the blood vessel by pressing down on the patient's skin over the blood vessel, distal to the introducer needle and the catheter. This finger pressure momentarily occludes the vessel, minimizing further blood flow through the introducer needle and the catheter.

The operator may then withdraw the introducer needle from the catheter. In some cases, the introducer needle is withdrawn into a needle tip cover or needle cover that extends over the needle tip and prevents accidental needle sticks. In general, a needle tip cover includes a casing, a sleeve, or another similar device that is designed to trap/capture the tip of the needle when the introducer needle is withdrawn from the catheter and the patient. After the needle is withdrawn, the catheter is left in place to provide intravenous access to the patient.

The separation of the introducer needle assembly from the catheter portions of the catheter assembly presents numerous potential hazards to the operator of the catheter device and others in the area. As indicated above, there is a risk of accidental needle sticks if the needle tip is not properly secured in a needle tip shield. Additionally, because the needle has been in contact with blood in the patient's vasculature, blood is often present on the needle's exterior as well as inside the lumen of the needle. As the needle is withdrawn from the catheter, there is a risk that this blood will drip from the needle tip or come into contact with other surfaces to expose people and equipment to blood. It has also been observed that withdrawing a needle from a catheter assembly often imparts energy to the parts of the needle assembly. For instance, during needle withdrawal, bending forces can be applied (either unintentionally or intentionally) to the needle. Such energy has been observed to cause blood to splatter or spray from the needle when the needle vibrates and shakes as it becomes free from the catheter assembly and releases the stored energy.

The present disclosure discusses a needle with a bi-directionally engageable crimp feature that allows the needle to be locked in a shielded position so as to significantly limit or prevent accidental sticks and blood exposure after the needle is withdrawn from a catheter assembly.

BRIEF SUMMARY OF THE INVENTION

The present application relates to a needle that is designed to overcome some of the limitations known in the art. Typically, the needle has a sharp or relatively sharp distal tip and an elongated tubular portion that has a substantially constant outer diameter ("OD"). Additionally, the needle has a crimp feature that has a maximum OD that is greater than the OD of the needle. The crimp feature, in turn, is configured to be bi-directionally engageable with any suitable capture mechanism that is capable of trapping the crimp feature and restricting the feature's proximal and distal movements with respect to the capture mechanism. Accordingly, where the needle is used in a catheter assembly comprising a needle shield, the needle may be retracted from an unshielded position and be locked into a shielded position that prevents the needle from sticking a person or exposing a person to blood from the needle.

The crimp feature may have any component or characteristic that allows it to be bi-directionally engaged with a capture mechanism. In some instances, the crimp feature comprises a proximal engagement, or a surface that is configured to contact a corresponding proximal cannula feature mating component in the capture mechanism to stop the needle from being further withdrawn through the capture mechanism in a proximal direction. In one example of a suitable proximal engagement, the proximal side of the crimp feature has a surface that broadens from the needle's OD to the crimp feature's maximum OD. In other words, at least one surface of the crimp feature's proximal side extends laterally past the needle's OD. The laterally extending surface(s) of the crimp feature's proximal side prevent the crimp feature from passing proximally through a proximal mating component that is sized to allow the needle, but not the lateral extending surfaces of the feature, to pass therethrough. Some examples of suitable proximal mating components include a washer or another object with an opening that is large enough to allow the needle, but not the crimp feature, to pass proximally therethrough.

In some instances, the crimp feature also comprises a distal engagement, or a surface that is configured to contact a corresponding distal cannula feature mating component in the capture mechanism to stop the needle from moving distally out of a needle shield, once the needle has been moved into a shielded position. The distal engagement may comprise any component that allows it to fulfill its intended purpose. Some examples of suitable distal engagements may comprise one or more notches, and/or one-directional barbs.

Where the distal engagement comprises one or more notches, the notches can have any suitable component that allows them to restrict the needle's distal movement in the capture mechanism after the needle has been moved to the shielded position. In one example, a notch comprises a distal contact surface that extends laterally past the OD of the needle. This distal contact surface is adapted to contact the distal mating component of the capture mechanism and prevent the crimp feature from translating past the distal mating component after the needle has been retracted into a needle shield.

Where the notch's distal contact surface extends laterally past the OD of the needle, the contact surface may extend away from a longitudinal axis of the needle at any angle that allows the contact surface to contact the distal mating component and restrict the needle's distal movement. Indeed, in one example, the distal contact surface runs substantially perpendicular to the needle's longitudinal axis.

While the distal contact surface may extend laterally past the OD of the needle at any location in the crimp feature, in some instances, the distal contact surface is disposed distal to the maximum diameter of the crimp feature. Accordingly, a portion of the crimp feature extends laterally past the lateral-most part of the distal contact surface. Thus, the crimp feature prevents the distal contact surface from scraping and/or skiving the interior of the capture mechanism before the distal contact surface contacts the mechanism's distal mating component.

Where the crimp feature comprises a notch with a distal contact surface that extends laterally past the needle's OD, the notched crimp feature may be formed in any suitable manner. In one example, the crimp feature is formed before the notch. In a second example, the notch is formed before the crimp feature. In a final example, a notch that partially penetrates through a wall of the needle is formed and then the needle is crimped at or near the partial notch. In this example, the partial notch may become fractured under the pressure from the crimping process.

While the described bi-directionally engageable cannula crimp feature can be particularly useful in the area of introducer needles and catheter assemblies, the skilled artisan will appreciate that such a crimp feature can be used in conjunction with a variety of devices, including, but not limited to, other hypodermic needles and other cannula with a sharpened distal tip.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof, which are illustrated in the appended drawings. Understanding that these drawings depict only typical embodiments of the invention and are not, therefore, to be considered to be limiting of its scope, the invention will be described and explained with additional specificity and detail through the use of the accompanying drawings in which:

FIG. 6 illustrates a perspective view of a representative embodiment of a needle comprising a bi-directionally engageable crimp feature having two notches;

FIGS. 8A-8B illustrate perspective views of some embodiments of a needle comprising a bi-directionally engageable crimp feature;

FIGS. 9A-9D illustrate plan views of a needle at different stages of a representative embodiment of a process for forming a bi-directionally engageable crimp feature;

FIG. 10A illustrates a plan view of a representative embodiment of a needle with notches that extend partially through the needle's wall;

FIG. 10B illustrates a perspective view of a representative embodiment of a needle with notches that extend partially through the needle's wall;

FIG. 10C illustrates a perspective view of a representative embodiment of a punch for forming notches that extend partially through a needle's wall;

FIG. 10D illustrates a plan view of a representative embodiment of a needle with partial notches formed by the punch in 10C punch;

FIG. 10E illustrates a perspective view of a portion of a representative embodiment of a needle comprising a crimp feature with a fractured notch; and FIG. 11A illustrates a perspective view of a representative embodiment of a needle comprising a bi-directionally engageable crimp feature that is in an unshielded position; and FIG. 11B illustrates a perspective view of a representative embodiment of a needle comprising a bi-directionally engageable crimp feature that is bi-directionally engaged with a split housing enclosure and a washer.

DETAILED DESCRIPTION OF THE INVENTION

The presently preferred embodiments of the described invention will be best understood by reference to the Figures, wherein like parts are designated by like numerals throughout. It will be readily understood that the components of the present invention, as generally described and illustrated in the Figures herein, could be arranged and designed in a wide variety of different configurations. Thus, the following more detailed description of the embodiments of the bi-directionally engageable cannula crimp feature, as represented in FIGS. 1 through 11B, is not intended to limit the scope of the invention, as claimed, but is merely representative of some presently preferred embodiments of the invention.

Generally, this application relates to a cannula comprising a bi-directionally engageable crimp feature. In other words, this application discusses a cannula with a crimp feature that is configured to be captured by a crimp feature capture mechanism in a manner that restricts the cannula from translating distally or proximally relative to the capture mechanism. Accordingly, the cannula can be retracted from an unshielded position in which the cannula tip is exposed and be bi-directionally locked within a protective shield to prevent unintended sticking and/or blood exposure.

As used herein, the terms "cannula" or "cannulae" may refer to virtually any rigid tube or tubes that are configured to be inserted into an animal's body to draw off or to introduce fluid, wherein the tube comprises a sharpened tip that allows the tube to puncture the body and access an intended space.

Some examples of such cannulae comprise hypodermic needles, cannulae capable relieving pressure from the bowels of bloated animals (e.g., cows), cannulae capable of inserting objects (e.g., RFID tags) into an animal, and other cannulae that may expose their operator to the risk of unintended sticking or blood exposure.

Where the cannula comprises a hypodermic needle, the cannula may comprise any suitable type of hypodermic needle, including an introducer needle for use in an IV catheter assembly (e.g., an over-the-needle peripheral IV catheter assembly. To provide a better understanding of the bi-directionally engageable cannula crimp feature, the feature is described below with reference to an introducer needle.

Figure 1:
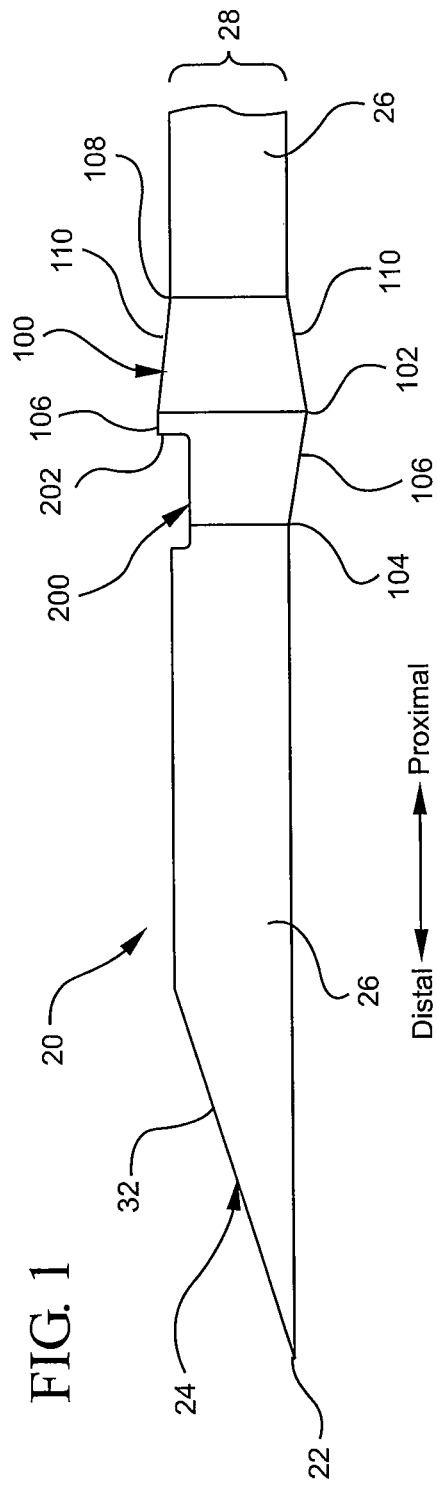
FIG. 1 illustrates a perspective view of a representative embodiment of a needle comprising a bi-directionally engageable crimp feature.

The introducer needle may have any component that is suitable for use with an IV catheter assembly. For instance, FIG. 1 shows a representative embodiment in which the introducer needle 20 comprises a sharpened distal tip 22, a lumen 24, an elongated tubular portion 26 having a substantially constant outer diameter ("OD") 28, and a bi-directionally engageable crimp feature 100. Moreover, each component of the needle may have any suitable characteristic. For example, the sharpened tip of the needle may comprise a standard bevel, a short bevel, a true short bevel, a bias grind point, a vet point, a lancet point, a deflected point (anti-coring), or another suitable known or novel needle point. Additionally, the lumen and elongated tubular portion may be any suitable size. For example, the needle may be any length or gauge (e.g., from a 7 to a 33 on the Stubs scale) that allows it to be used as the introducer needle in an IV assembly.

The crimp feature may comprise any component or characteristic that allows it to be bi-directionally engaged by a crimp feature capture mechanism (discussed hereinafter). Indeed, in some embodiments, the crimp feature is shaped to have a maximum OD that is greater than the needle's OD. For example, FIG. 1 illustrates a needle 20, which has been pinched from two sides to form the crimp feature 100 having a maximum OD 102 that is greater than the needle's OD 28. Additionally, FIG. 1 shows that, from its distal end 104, the crimp feature 100 broadens proximally towards the feature's maximum OD 102 so that the feature 100 comprises at least one distal surface 106 that extends laterally past the needle's OD 28. Similarly, FIG. 1 shows that from its proximal end 108, the crimp feature 100 broadens distally towards the feature's maximum OD 102 so that the feature 100 comprises at least one proximal surface 110 that extends laterally past the needle's OD 28. While FIG. 1 shows one representative embodiment of the crimp feature 100, the skilled artisan will recognize that the crimp feature may have a variety of other shapes and still have a maximum diameter that is greater than the OD of the needle.

The crimp feature comprises at least one proximal engagement that is configured to contact a corresponding cannula feature mating component (the "proximal mating component") (discussed hereinafter) of a capture mechanism. The proximal engagement can comprise any suitable surface that is configured to contact the proximal mating component in a manner that prevents the needle from moving proximally with respect to the capture mechanism. Some examples of suitable proximal engagements may include the larger OD of the crimp feature's proximal side (e.g., one or more laterally extending proximal surfaces), one or more one-way barbs, one or more notches, and/or other suitable structures that provide the crimp feature with a surface configured to contact the proximal mating component in a manner that stops the feature from moving proximally in the capture mechanism.

FIG. 1 shows that, in at least some embodiments, the feature's laterally extending proximal surfaces 110 act as the feature's proximal engagement. Such a proximal engagement may prevent the feature from passing proximally through a proximal mating component that is sized to allow the needle, but not the laterally extending proximal surface, to pass therethrough.

Figure 2:
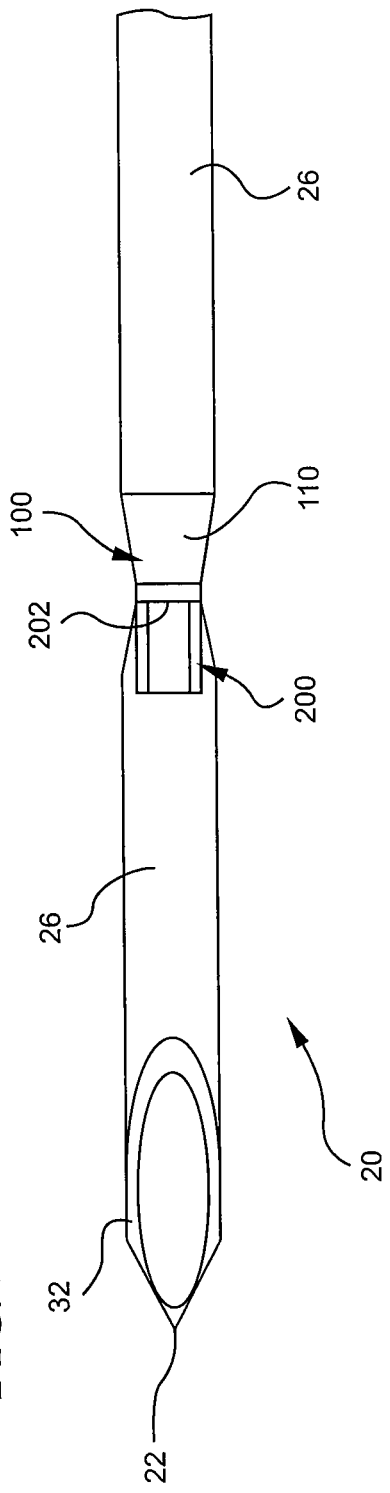
FIG. 2 illustrates a perspective view of a representative embodiment of the needle from FIG. 1.

The crimp feature also comprises at least one distal engagement that is configured to contact a corresponding distal cannula feature mating component (the "distal mating component") (discussed hereinafter) in the capture mechanism, once the needle has been retracted from the catheter assembly and into a shielded position. The distal engagement may comprise any suitable surface that is configured to contact the distal mating component of the capture mechanism in a manner that prevents the needle from moving distally with respect to the distal mating component. For instance, the distal engagement may comprise one or more notches, one-directional barbs, and/or other similar components. By way of illustration, FIGS. 1 and 2 show different views of a representative embodiment in which the distal engagement of the crimp feature 100 comprises a notch 200.

Where the distal engagement comprises a notch, the notch may have any characteristic that allows it to engage the distal mating component once the crimp feature has been retracted into the capture mechanism. For instance, from a face view of the notch, the notch may have any shape that allows it act as a distal engagement, including a shape that is substantially rectangular, square, triangular, polygonal, irregular, etc. By way of illustration, FIG. 2 shows a perspective view of cannula feature 100 in which the notch 200 appears substantially rectangular in shape.

In some embodiments, the notch comprises one or more distal contact surfaces that are configured to contact the distal mating component and prevent the needle from moving distally respective to the mating component. While the notch may comprise any suitable distal contact surface, FIG. 3 shows a representative embodiment in which the notch 200 comprises a distal contact surface 202 that extends laterally past the OD 28 of the needle 20.

Figure 3:
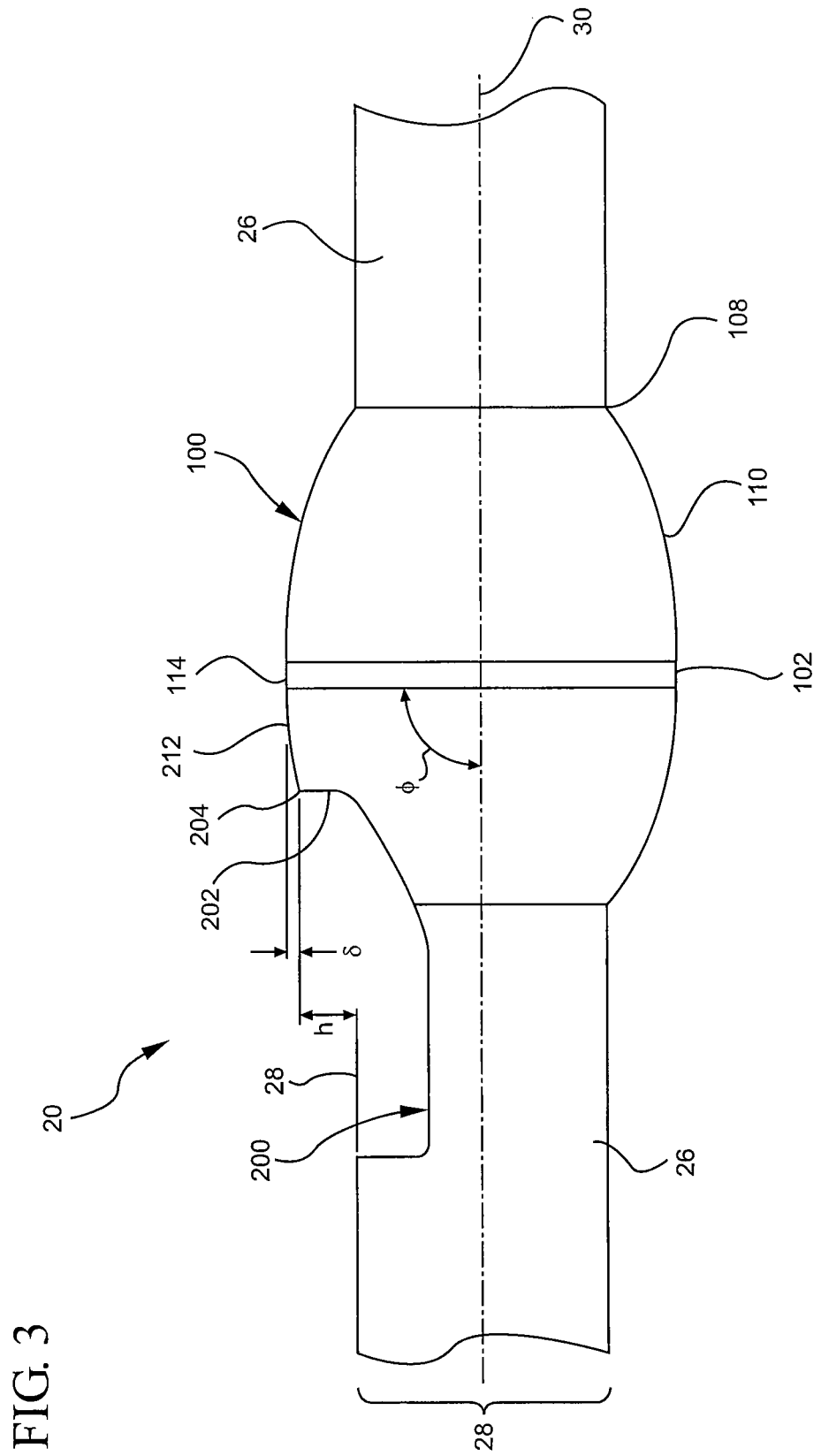
FIG. 3 illustrates a plan view of a representative embodiment of a portion of a needle comprising a bi-directionally engageable crimp feature.
Figure 4:
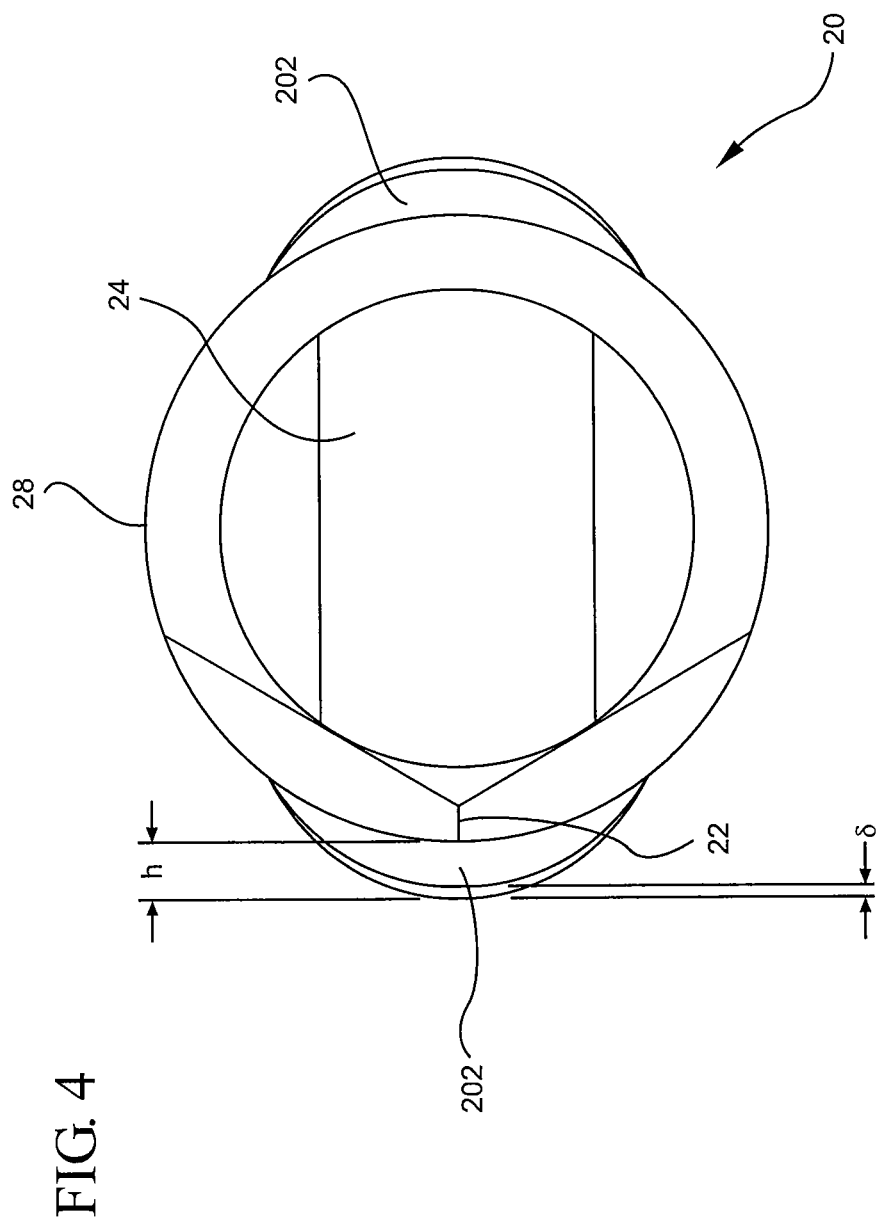
FIG. 4 illustrates a perspective view of a representative embodiment of a needle comprising a bi-directionally engageable crimp feature having two notches.

In embodiments where the distal contact surface extends laterally past the needle's OD, FIG. 3 shows the distal contact surface 202 may extend any suitable distance h (see also FIG. 4) that allows the distal contact surface 202 to act as the distal engagement.

In some embodiments where the distal contact surface extends laterally past the needle's OD, the notch is configured so that the contact surface is non-skiving. For instance, FIG. 3 shows that a portion 212 of the crimp feature 100 can extend laterally past the contact surface's 202 lateral-most end 204 so that a lateral-most edge 114 of the crimp feature 100 prevents the contact surface 202 from scraping the capture mechanism before the contact surface 202 engages the distal mating component (not shown). In such instances, the distance (as shown as δ in FIG. 3) between the contact surface's lateral-most end 204 and the crimp feature's lateral-most edge 114 may be any suitable distance.

Where the distal contact surface extends laterally past the needle's OD, at least a portion, if not all, of the contact surface may extend away from a longitudinal axis of the needle at any angle that allows the contact surface to act as the feature's distal engagement. However, where the contact surface extends away from the needle's longitudinal axis at an angle of about 90 degrees or less, the contact surface may act to catch and/or dig into the distal mating component better than it would at an angle much larger than about 90 degrees. Accordingly, in some embodiments, the angle between the needle's longitudinal axis and at least a portion of the contact surface is between about 25 and about 105 degrees. In other embodiments, the angle between the needle's longitudinal axis and the contact surface is between about 60 and about 100 degrees. In still other embodiments, the angle between the needle's longitudinal axis and the contact surface is between about 85 and about 95 degrees. By way of illustration, FIG. 3 shows a representative embodiment in which the angle θ between the needle's longitudinal axis 30 and the distal contact surface 202 is about 90 degrees ±5 degrees.

Figure 5:
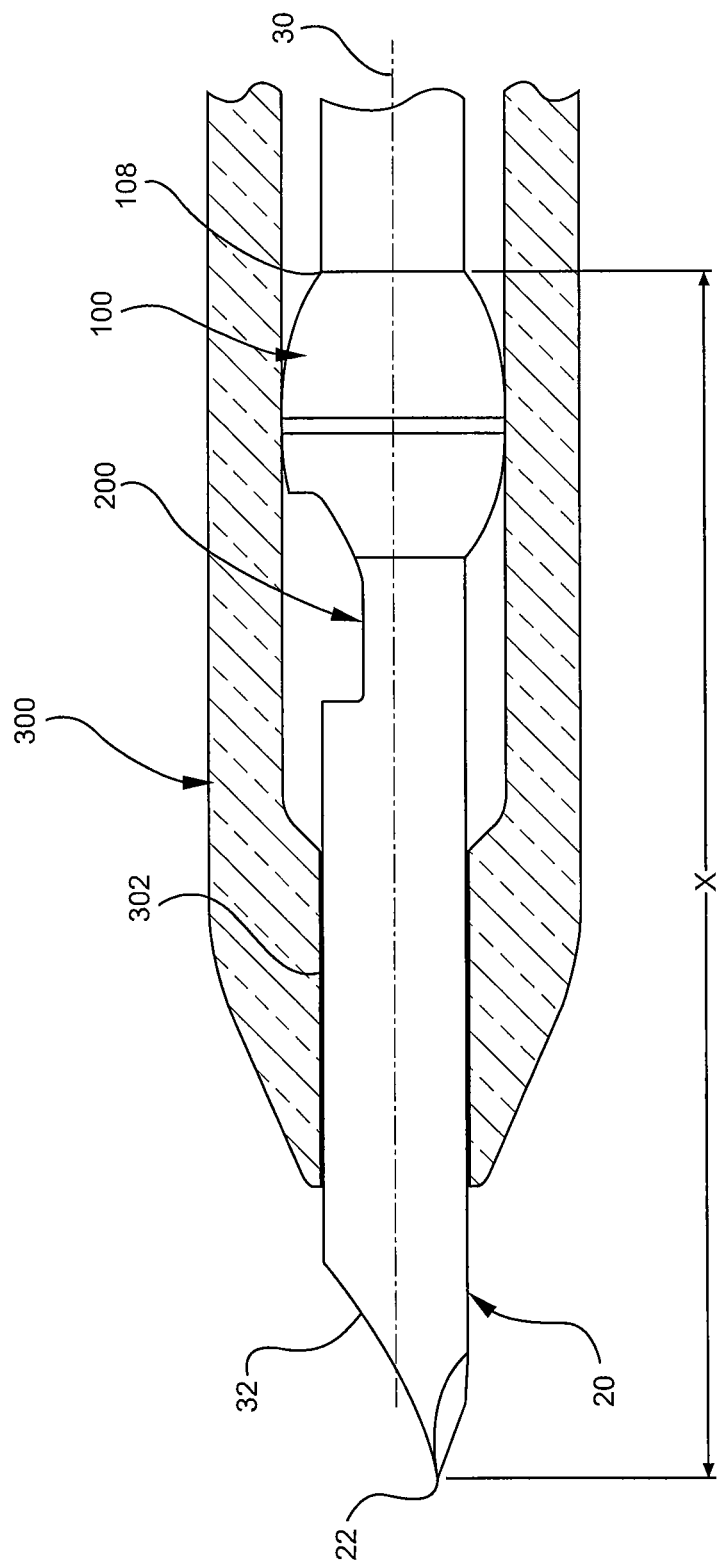
FIG. 5 illustrates a plan view of a representative embodiment of a needle comprising a bi-directionally engageable crimp feature, wherein the tip of needle extends beyond a distal catheter tip of an over-the-needle peripheral IV catheter in which the IV catheter is partially cutaway.

In embodiments where the crimp feature comprises a notch that acts as the distal engagement, the entire notched crimp feature (e.g., crimp feature 100 with notch 200) may be located any suitable distance from the needle's distal tip that allows the needle to be used with a catheter assembly. By way of illustration, FIG. 5 shows that the notched crimp feature 100/200 may be disposed on the needle 20, adjacent to a distal seal 302 of the catheter 300. More specifically, FIG. 5 shows the distance x between the needle's distal tip 22 and the feature's proximal end 108 can be any suitable distance that allows the cannula feature 100 to be disposed distal to the catheter's distal seal 302. Indeed, in some embodiments, the distance x between the needle's distal tip 22 and the feature's proximal end 108 is selected from a distance of a less than about 10 millimeters, less than about 8 millimeters, and less than about 6 millimeters.

In embodiments where the crimp feature comprises a notch, the notch may have any orientation with respect to the needle's bevel that allows the notch to fulfill its intended purpose. For instance, the notch can be disposed in the crimp feature so as to face in substantially the same direction as, an opposite direction to, or in another suitable direction with respect to the needle's bevel. For example, FIG. 5 shows an embodiment in which the notch 200 faces in substantially the same direction as the needle's bevel 32.

Where the bi-directionally engageable crimp feature comprises a notched crimp feature, the feature may comprise any suitable number of notches. For example, FIG. 5 shows an embodiment in which the crimp feature 100 comprises a single notch 200. However, FIG. 6 shows a representative embodiment in which the crimp feature comprises 2 notches 200. In still other embodiments, which are not shown, the crimp feature may comprise more than two notches. For instance, where the crimp feature is bent to have 3 or 4 surfaces that extend laterally past the needle's OD, the crimp feature can have 3 or 4 notches, respectively.

Figure 7A:
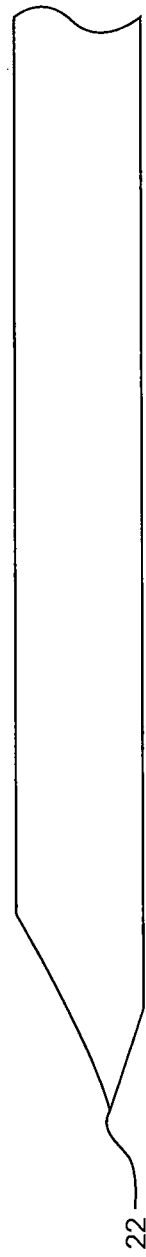
FIGS. 7A-7D illustrate plan views of a needle at different stages of a representative embodiment of a processes for forming a bi-directionally engageable crimp feature.
Figure 7B:
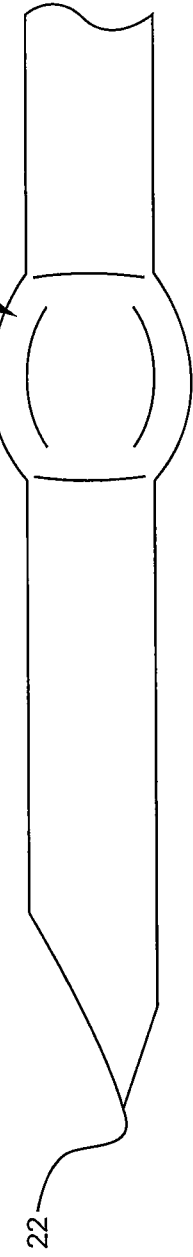

In embodiments where the bi-directionally engageable crimp feature comprises a notched crimp feature, the feature may be made in any suitable manner. In one example, FIGS. 7A through 7D illustrate a representative embodiment of a process for forming the notched crimp by forming the crimp before forming the notch. Specifically, FIG. 7A shows this crimp/notch-notched crimp is formed by providing a needle 20 with a sharpened tip 22. FIG. 7B shows the process continues by pinching the sides of the needle 20 to form the crimp feature 100. This pinching can be accomplished in any suitable manner, including through the use of opposing needle anvils.

Figure 7C:
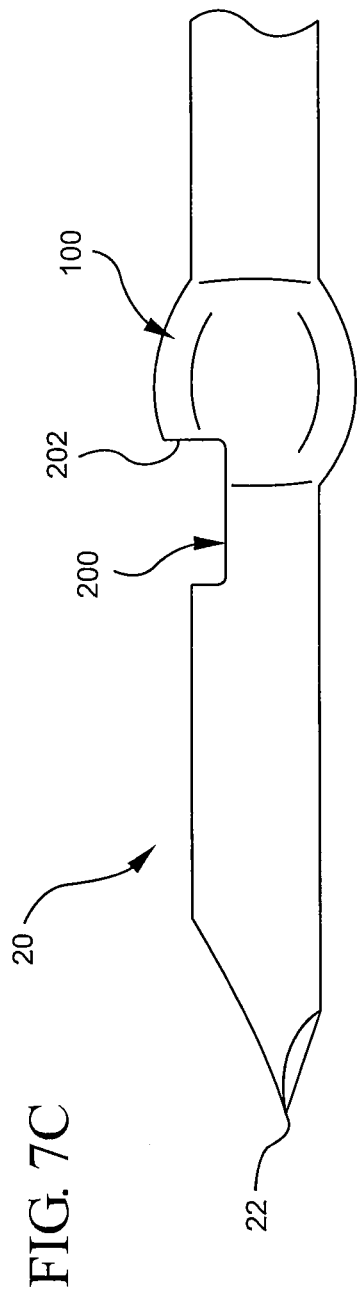
Figure 7D:
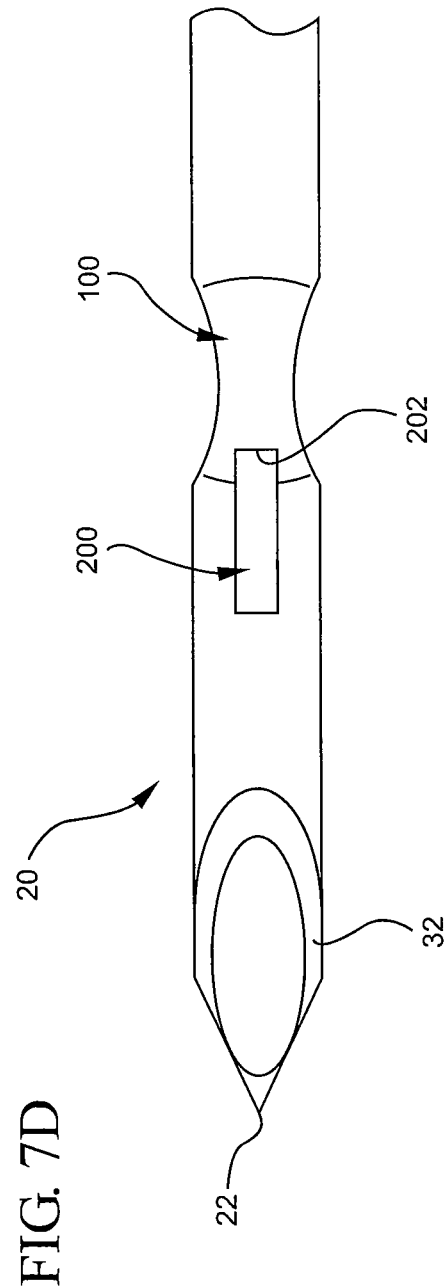

Once the crimp feature 100 has been formed, FIGS. 7C and 7D show the notch 200 can be placed in the crimp feature 100 to form a notched crimp feature. The notch can be formed in the crimp feature in any known or novel manner, including through the use of electrical discharge machining, grinding, punching, filing, etching, or another notching process. Because the notch in this process is formed after the crimp, FIGS. 7C and 7D show that where the notch retains its original shape (e.g., square or rectangular) once it is placed in the needle.

Figure 9C:
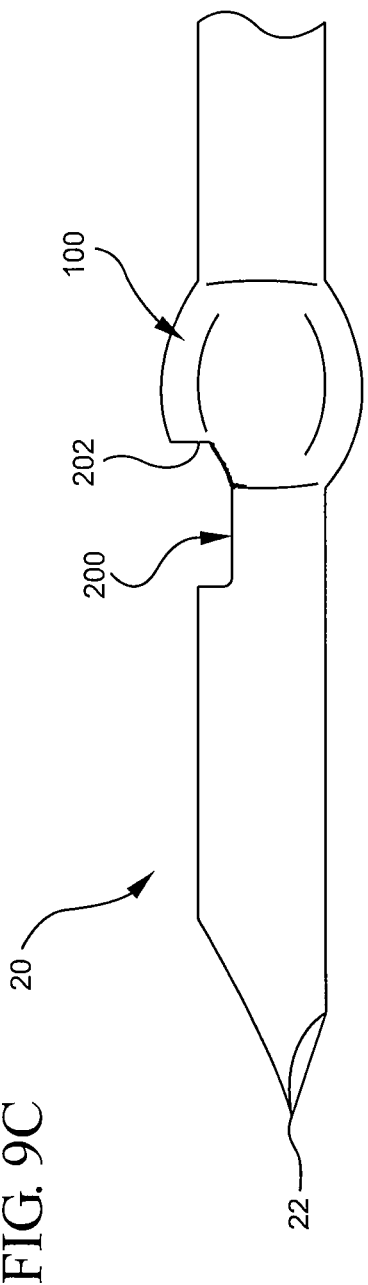
Figure 9D:
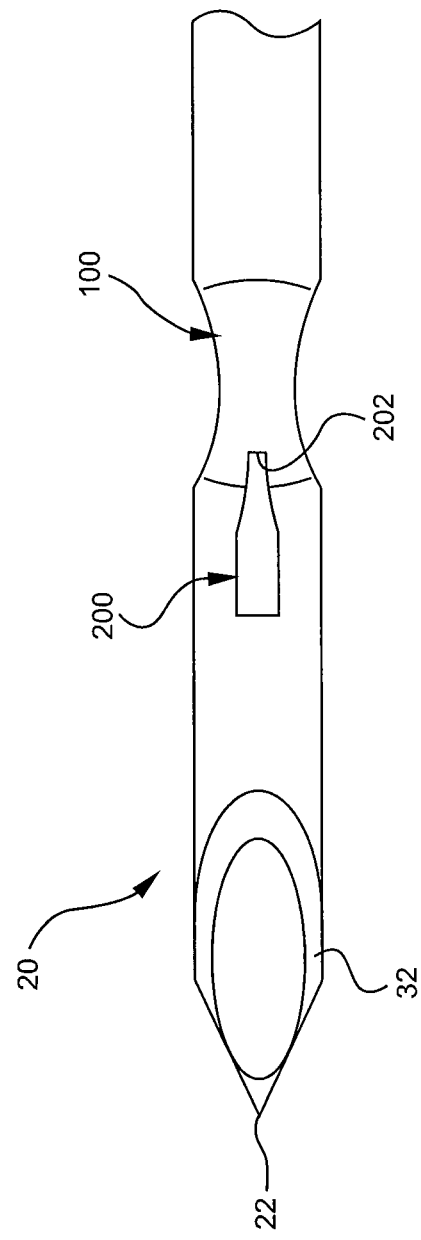

In contrast, FIGS. 8A through 8B illustrate some embodiments of the notched crimp feature 100/200 in which the shape of the notch 200 is changed during the feature's formation. One example of a method of forming the notched crimp features from FIGS. 8A and 8B is shown in FIGS. 9A through 9D. Specifically, FIGS. 9A-9D illustrate a representative embodiment of a process for forming the notch before the crimp. In particular, FIG. 9A shows this notch/crimp-notched crimp is formed by providing a needle 20 with a sharpened tip 22. FIG. 9B shows the process continues by forming a notch 200 in the needle 20 in any suitable manner. After the formation of the notch 200, FIGS. 9C and 9D show the needle 20 may be crimped to form the notched crimp feature 100/200. Of note, FIGS. 9B through 9D show that shape of the proximal end of the notch 200 is altered by the crimping process.

In a final non-limiting example of a method for forming a needle 100 comprising the notched crimp 100/200, FIGS. 10A through 10D illustrate a process in which a partial notch is formed in the needle before the needle is crimped. Specifically, FIGS. 10A and 10B show this partial notch/crimp-notched crimp is formed by forming a partial notch 206, which does not completely penetrate the needle's wall, in the needle 20. The partial notch may be formed in any known or novel manner, including by punching, filing, etching, grinding, or another method that is capable for forming a notch that only partially extends through the needle's wall. For instance, FIG. 10C illustrates one example of a suitable punch 400 and FIG. 10D illustrates the needle 20 after the punch 400 has formed partial notches 206 in the needle's walls.

After the partial notches 206 have been formed in the needle 20, FIG. 10E shows the needle 20 is crimped to form the notched crimp 100/200. FIG. 10E also illustrates that as part of the crimping process, the partial notch (206 in FIG. 10B) is fractured to form a fractured notch 208.

The described bi-directionally engageable crimp feature (e.g., the notched crimp feature 100/200) may be used with any suitable capture mechanism that is capable of trapping the bi-directionally engageable crimp feature and limiting the feature's distal and proximal movement respective to the capture mechanism. In some embodiments, as previously mentioned, a suitable bi-directional needle feature capture mechanism comprises a distal mating component and a proximal mating component.

In such embodiments, the distal mating component may be any structure that is adapted to contact the crimp feature's distal engagement (e.g., the notch's distal contact surface 202) and limit the feature's distal movement once the needle has been moved to a shielded position. For instance, FIG. 11A illustrates that the distal mating component may comprise one or more biased structures 500 (e.g., portions of a split housing enclosure), which may be any suitable structure that presses towards the needle 20. Accordingly, FIG. 11B illustrates that when the notched crimp feature 100/200 is moved proximally past distal mating component (e.g., the biased structures 500), the mating component moves to a position that blocks the crimp feature's distal engagement (e.g., the distal contact surface 202). In this manner, the distal mating component(s) prevents the feature 100 from moving proximally past the distal mating component (e.g., the biased structures 500).

The proximal mating component of the capture mechanism may comprise any component that is adapted to contact the crimp feature's proximal engagement (e.g., a proximal surface 110 of the crimp feature that extends laterally past the needle's OD) and limit the feature's proximal movement once the needle has been moved to a shielded position (shields not shown). For instance, as previously mentioned, the proximal mating component may be any suitable component that has an opening sized to allow the needle, but not the laterally extending surfaces of the crimp feature's proximal side, to pass therethrough. By way of illustration, FIG. 11A illustrates a representative embodiment in which the proximal mating component comprises a rigid washer 600. FIG. 11B illustrates that when the needle 20 is moved from the unshielded position (shown in FIG. 11A) to the shielded position, the proximal surfaces 110 of the crimp feature 100 that extend laterally past the needle's OD 28 are too large to pass through the inner diameter of the washer 600.

Thus, once the bi-directionally engageable crimp feature (e.g., the notched crimp 100/200) is moved between the capture mechanism's distal and proximal mating component (e.g., biased structures 500 and washer 600, respectively), the crimp feature becomes irreversibly trapped. Thus, where the needle is used in conjunction with a needle shield, the needle is locked in the shielded position for proper disposal.

In addition to aforementioned benefits, the described bi-directionally engageable crimp feature may offer several additional benefits. For instance, because the crimp feature itself can be bi-directionally captured, needles comprising the described crimp feature do not require known methods of transverse tip barrier protection. Instead, such transverse barrier tip protection may optionally be used to provide redundant needle tip protection.

Because the described crimp feature may comprise a notch (e.g., notch 200), the crimp feature may also allow an operator to see "flashback" when the catheter is placed in a patient's blood vessel. For instance, where the needle is placed within another device (e.g., a catheter) and the needle is inserted into a patient's vasculature, blood flows through the needle's lumen, exits the lumen through the notch, and travels between the outer diameter of the lumen and the inner diameter of the other device (e.g., the catheter). Accordingly, where the other device is at least partially transparent, an operator may visualize a small amount of blood and, thereby, confirm placement of the catheter within a patient's blood vessel.

Moreover, because the described bi-directionally engageable crimp feature can comprise a notched crimp, a flashback notch and capture feature may be disposed closer to the needle's tip than would be possible in certain prior art devices. Accordingly, a needle comprising the notched crimp can be protected with a shorter needle shield than may certain prior art needles.

The present invention may be embodied in other specific forms without departing from its structures, methods, or other essential characteristics as broadly described herein and claimed hereinafter. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A cannula with a bi-directionally engageable crimp feature for preventing the cannula from protruding from a cannula shield once the cannula is withdrawn into the cannula shield, the cannula comprising:
    an elongated tubular portion having a proximal end and a distal end, the distal end comprising a sharpened distal tip;
    a crimp feature formed between a first and a second location on the elongated tubular portion of the cannula, the first location being distal to the second location, wherein the outside diameter of the elongated tubular portion at the first location is a first outside diameter and the outside diameter of the elongated tubular portion at the second location is a second outside diameter, the crimp feature comprising an expansion of the outside diameter of the cannula from both the first outside diameter at the first location and the second outside diameter at the second location to a maximum outside diameter at a third location on the elongated tubular portion, the third location being between the first and second locations, the maximum outside diameter being greater than the first and the second outside diameters; and
    a notch at least partially disposed within the crimp feature, the notch having a distal end and a proximal end, the proximal end of the notch being at a fourth location on the elongated tubular portion of the cannula, the fourth location being between the first and the third locations such that the outside diameter of the crimp feature at the fourth location is less than the maximum outside diameter at the third location but greater than the first outside diameter at the first location.

2. The cannula of claim 1, wherein the notch comprises a contact surface that that defines a proximal edge of the notch.

3. The cannula of claim 2, wherein the contact surface extends away from a longitudinal axis of the cannula at an angle between about 25 and about 105 degrees.

4. The cannula of claim 3, wherein the contact surface runs substantially perpendicular to the longitudinal axis of the cannula.

5. The cannula of claim 2, wherein the contact surface is non-skiving.

6. The cannula of claim 2, wherein the notch is approximately axially aligned with a bevel of the cannula.

7. The cannula of claim 1, wherein the first and the second outside diameters are the same.

8. A catheter assembly, comprising:
    a catheter assembly having a bi-directional needle feature capture mechanism; and
    a hypodermic needle with a bi-directionally engageable crimp feature for preventing the needle from protruding from the catheter assembly once the needle is withdrawn into the catheter assembly, the needle comprising:
        an elongated tubular portion having a proximal end and a distal end, the distal end comprising a sharpened distal tip;
        a crimp feature formed between a first and a second location on the elongated tubular portion of the needle, the first location being distal to the second location, wherein the outside diameter of the elongated tubular portion at the first location is a first outside diameter and the outside diameter of the elongated tubular portion at the second location is a second outside diameter, the crimp feature comprising an expansion of the outside diameter of the needle from both the first outside diameter at the first location and the second outside diameter at the second location to a maximum outside diameter at a third location on the elongated tubular portion, the third location being between the first and second locations, the maximum outside diameter being greater than the first and the second outside diameters; and
        a notch at least partially disposed within the crimp feature, the notch having a distal end and a proximal end, the proximal end of the notch being at a fourth location on the elongated tubular portion of the needle, the fourth location being between the first and the third locations such that the outside diameter of the crimp feature at the fourth location is less than the maximum outside diameter at the third location but greater than the first outside diameter at the first location.

9. The assembly of claim 8, wherein the distal end of the notch comprises a contact surface which extends away from a longitudinal axis of the needle at an angle between about 85 and about 95 degrees.

10. The assembly of claim 8, wherein the capture mechanism comprises 1) a proximal mating component having an opening through which the needle slides, the opening having an internal diameter that is less than the maximum outside diameter of the crimp feature that prevents the crimp feature of the needle from sliding through the opening in the proximal mating component, and 2) a distal mating component that is inserted into the notch when the needle is inserted sufficiently into the catheter assembly.

11. The assembly of claim 10, wherein the proximal mating component comprises a rigid washer and the distal mating component comprises a biased structure.

12. An IV catheter assembly comprising:
a catheter;
a needle shield; and
a needle with a bi-directionally engageable crimp feature for preventing the needle from protruding from the needle shield once the needle is withdrawn into the needle shield, the needle comprising:
an elongated tubular portion having a proximal end and a distal end, the distal end comprising a sharpened distal tip;
a crimp feature formed between a first and a second location on the elongated tubular portion of the needle, the first location being distal to the second location, wherein the outside diameter of the elongated tubular portion at the first location is a first outside diameter and the outside diameter of the elongated tubular portion at the second location is a second outside diameter, the crimp feature comprising an expansion of the outside diameter of the needle from both the first outside diameter at the first location and the second outside diameter at the second location to a maximum outside diameter at a third location on the elongated tubular portion, the third location being between the first and second locations, the maximum outside diameter being greater than the first and the second outside diameters; and
a notch at least partially disposed within the crimp feature, the notch having a distal end and a proximal end, the proximal end of the notch being at a fourth location on the elongated tubular portion of the needle, the fourth location being between the first and the third locations such that the outside diameter of the crimp feature at the fourth location is less than the maximum outside diameter at the third location but greater than the first outside diameter at the first location.

13. The IV catheter assembly of claim 12, wherein the needle shield includes a washer having an internal opening diameter that is greater than the second outside diameter of the needle but less than the maximum outside diameter of the crimp feature thereby allowing the needle to slide proximally within the washer when retracted into the needle shield until the crimp feature reaches the washer.

14. The IV catheter assembly of claim 12, wherein the needle shield includes a biased structure that is inserted into the notch when the needle is slid proximally into the needle shield.

15. The IV catheter assembly of claim 12, wherein the notch penetrates into the lumen of the needle thereby allowing flashback to flow out of the needle into the catheter when the needle is inserted into a patient.

16. The IV catheter assembly of claim 12, wherein the needle further comprises another notch positioned on the needle opposite the notch.

17. The IV catheter assembly of claim 12, wherein the distal end of the notch is positioned distally to the first location of the crimp feature.

18. The IV catheter assembly of claim 12, wherein the first outside diameter and the second outside diameter are the same.

19. The IV catheter assembly of claim 12, wherein the proximal end of the crimp feature comprises a contact surface that is perpendicular to the longitudinal axis of the elongated tubular portion.

* * * * *